(12) United States Patent
Huang et al.

(10) Patent No.: US 9,857,576 B2
(45) Date of Patent: Jan. 2, 2018

(54) MULTI-SEGMENT OPTICAL COMPONENT AND RELATED OPTICAL DETECTING DEVICE CAPABLE OF INCREASING SNR

(71) Applicant: PixArt Imaging Inc., Hsin-Chu (TW)

(72) Inventors: Yu-Hsiang Huang, Hsin-Chu (TW); Hung-Ching Lai, Hsin-Chu (TW)

(73) Assignee: PixArt Imaging Inc., Hsin-Chu (TW)

( * ) Notice: Subject to any disclaimer, the term of this patent is extended or adjusted under 35 U.S.C. 154(b) by 190 days.

(21) Appl. No.: 14/981,921

(22) Filed: Dec. 29, 2015

(65) Prior Publication Data

US 2017/0059839 A1 Mar. 2, 2017

(30) Foreign Application Priority Data

Sep. 2, 2015 (TW) .............................. 104128947 A (51) Int. Cl.
*G02B 19/00* (2006.01)
*G02B 3/08* (2006.01)
*G01J 1/04* (2006.01)
*A61B 5/00* (2006.01)
*G01N 21/47* (2006.01)

(52) U.S. Cl.
CPC ........ *G02B 19/0085* (2013.01); *A61B 5/0059* (2013.01); *G01J 1/0422* (2013.01); *G01N 21/474* (2013.01); *G02B 3/08* (2013.01); *G02B 19/0009* (2013.01)

(58) Field of Classification Search
CPC .. G02B 19/0085; G02B 19/0009; G02B 3/08; G01J 1/0422; G01N 21/474; A61B 5/0059

USPC ................................. 250/227.28; 362/311.02
See application file for complete search history.

(56) References Cited

U.S. PATENT DOCUMENTS

| | | | |
|---|---|---|---|
| 7,251,084 B2 * | 7/2007 | Shimura ................. | F21V 5/045 359/742 |
| 8,220,975 B2 * | 7/2012 | Miyashita ................. | F21V 5/04 359/642 |
| 8,733,981 B2 * | 5/2014 | Jiang ........................ | F21V 5/04 362/311.01 |
| 2011/0286221 A1 * | 11/2011 | Saito ....................... | F21V 5/045 362/311.06 |

* cited by examiner

*Primary Examiner* — Seung C Sohn
(74) *Attorney, Agent, or Firm* — Winston Hsu (57) ABSTRACT

A multi-segment optical component applied to increase signal-to-noise ratio includes a base, a central lens portion, an isolating lens portion and a collecting lens portion. The central lens portion is disposed on center of the base. The isolating lens portion is disposed by a side of the central lens portion, and the collecting lens portion is disposed by the other side of the central lens portion opposite to the isolating lens portion. At least one of the isolating lens portion and the collecting lens portion has a curvature radius different from a curvature radius of the central lens portion, and the curvature radius of the isolating lens portion can be similar to or different from the curvature radius of the collecting lens portion. The central lens portion has a central axle which does not overlap a curvature center of one of the isolating lens portion and the collecting lens portion.

28 Claims, 7 Drawing Sheets

MULTI-SEGMENT OPTICAL COMPONENT AND RELATED OPTICAL DETECTING DEVICE CAPABLE OF INCREASING SNR

BACKGROUND OF THE INVENTION

1. Field of the Invention

The present invention relates to an optical detecting device utilizing an optical component to condense the light beam, and more particularly, to a multi-segment optical component capable of increasing signal-to-noise ratio and a related optical detecting device utilizing the multi-segment optical component.

2. Description of the Prior Art

Figure 1:
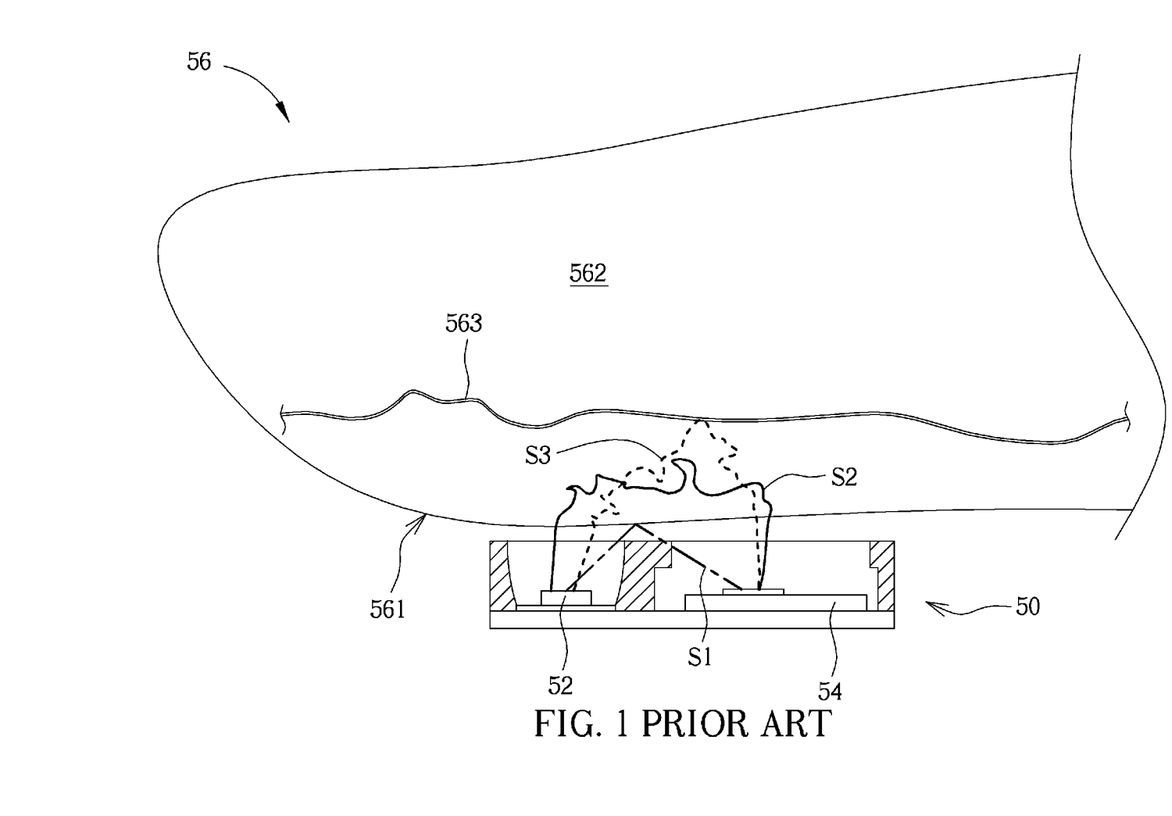
FIG. 1 is a diagram of an optical detecting device in prior art.
Figure 2:
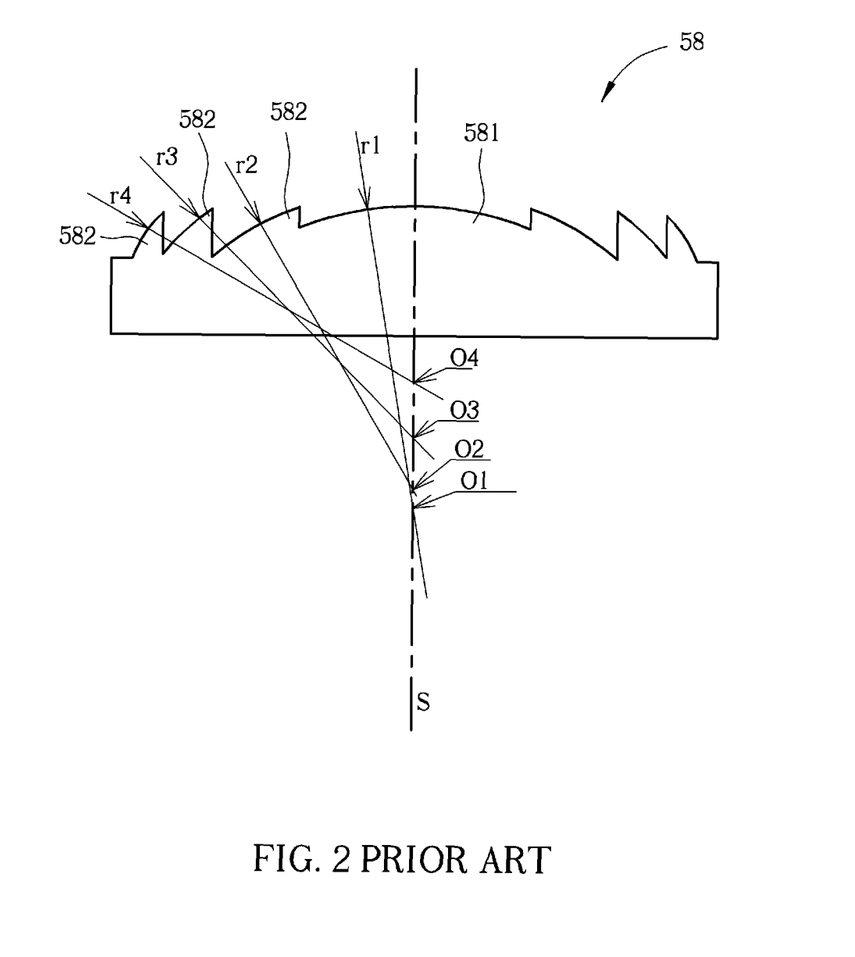
FIG. 2 is a sectional view of a conventional Fresnel lens.

Please refer to FIG. 1 and FIG. 2. FIG. 1 is a diagram of an optical detecting device 50 in prior art. FIG. 2 is a sectional view of a conventional Fresnel lens. The optical detecting device 50 utilizes a light emitting component 52 to output an optical detecting signal, the optical detecting signal is projected onto and reflected from an external object 56 to be received by an optical detecting component 54, and the optical detecting device 50 acquires information of the external object 56 by analyzing the reflected optical detecting signal. The external object 56 includes an epidermal layer 561, a dermis layer 562 and a vessel 563. As the external object 56 does not contact against a touch region of the optical detecting device 50, the optical detecting component 54 receives an epidermal scattering signal S1, a dermis scattering signal S2 and a vessel scattering signal S3. The dermis scattering signal S2 and the vessel scattering signal S3 is helpful to acquire the wanted information of the external object 56, and the epidermal scattering signal S1 is noise which decreases detection accuracy about the external object 56 analyzed by the optical detecting device 50.

The conventional Fresnel lens 58 is disposed above the light emitting component 52 to increase quantity of the optical detecting signal. The conventional Fresnel lens 58 is mainly composed of a central lens portion 581 and a plurality of lateral lens portions 582. A curvature radius r1 of the central lens portion 581 is substantially equal to curvature radii r2, r3, r4 of the lateral lens portions 582. A curvature center O1 of the central lens portion 581 and curvature centers O2, O3, O4 of the lateral lens portions 582 overlap a symmetry axis S of the central lens portion 581. The conventional Fresnel lens 58 cannot overcome noise interference resulted from the epidermal scattering signal S1; therefore, design of an optical detecting device capable of effectively eliminating the epidermal scattering signal to increase detection accuracy is an important issue in the related optical detection industry.

SUMMARY OF THE INVENTION

The present invention provides a multi-segment optical component capable of increasing signal-to-noise ratio and a related optical detecting device utilizing the multi-segment optical component for solving above drawbacks.

According to the claimed invention, a multi-segment optical component capable of increasing signal-to-noise ratio is disclosed. The multi-segment optical component includes a base, a central lens portion, a first isolating lens portion and a first collecting lens portion. The central lens portion is disposed on center of the base. The first isolating lens portion is disposed by a side of the central lens portion. The first collecting lens portion is disposed by the other side of the central lens portion opposite to the first isolating lens portion. At least one of the first isolating lens portion and the first collecting lens portion has a curvature radius different from a curvature radius of the central lens portion, and the curvature radius of the first isolating lens portion is similar to or different from the curvature radius of the first collecting lens portion. The central lens portion includes a central axle, and at least one of curvature centers of the first isolating lens portion and the first collecting lens portion does not overlap the central axle.

According to the claimed invention, an optical detecting device capable of increasing signal-to-noise ratio is disclosed. The optical detecting device includes a light emitting component, an optical detecting component and at least one multi-segment optical component. The light emitting component is adapted to emit an optical detecting signal toward an external object. The optical detecting component is adapted to receive an optical reflecting signal from the external object. The least one multi-segment optical component is disposed on the light emitting component and/or the optical detecting component, and adapted to condense the optical detecting signal and/or isolate part of the optical reflecting signal. The at least one multi-segment optical component includes a base, a central lens portion, a first isolating lens portion and a first collecting lens portion. The central lens portion is disposed on center of the base. The first isolating lens portion is disposed by a side of the central lens portion. The first collecting lens portion is disposed by the other side of the central lens portion opposite to the first isolating lens portion. At least one of the first isolating lens portion and the first collecting lens portion has a curvature radius different from a curvature radius of the central lens portion, and the curvature radius of the first isolating lens portion is similar to or different from the curvature radius of the first collecting lens portion. The central lens portion includes a central axle, and at least one of curvature centers of the first isolating lens portion and the first collecting lens portion does not overlap the central axle.

According to the claimed invention, when the at least one multi-segment optical component is disposed above the optical detecting component, the optical detecting component aligns with a region of the central lens portion near to the first isolating lens portion of the at least one multi-segment optical component. The at least one multi-segment optical component is disposed above a region of the light emitting component near to the optical detecting component.

The present invention provides the innovative multi-segment optical component distinct from the conventional Fresnel lens. All the lateral lens portions of the multi-segment optical component have curvature radii different from the curvature radius of the central lens portion, and the curvature centers of all the lateral lens portions do not overlap the central axle of the central lens portion. Therefore, the multi-segment optical component can utilize the scattering isolation module to prevent the epidermal scattering signal from being transmitted toward the optical detecting component, and further utilize the optical collection module to collect the vessel scattering signal and/or the dermis scattering signal, so as to effectively increase the signal-to-noise ratio of the optical detecting device; the optical detecting device of the present invention can acquire accurate detecting result even through the external object does not directly contact an effective region (the working region, the touch region) of the optical detecting device.

These and other objectives of the present invention will no doubt become obvious to those of ordinary skill in the art after reading the following detailed description of the preferred embodiment that is illustrated in the various figures and drawings.

DETAILED DESCRIPTION

Figure 3:
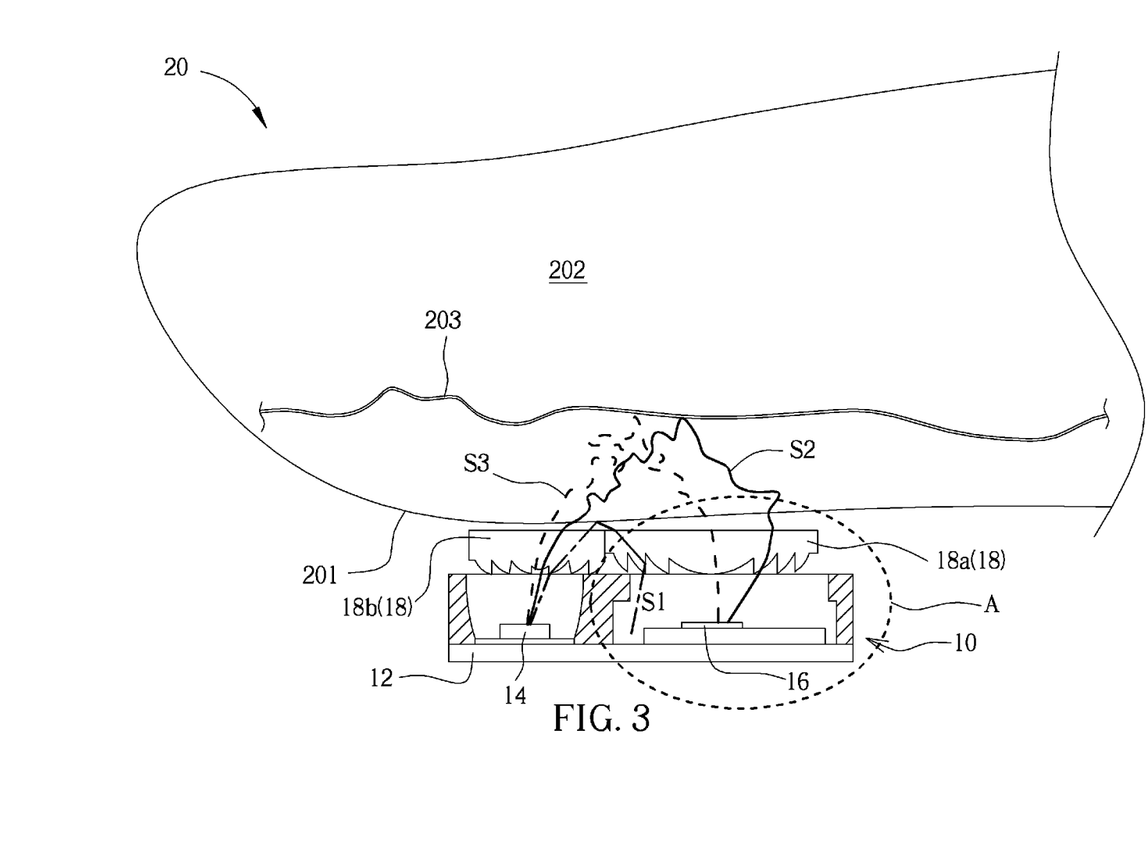
FIG. 3 is a diagram of an optical detecting device according to an embodiment of the present invention.
Figure 4:
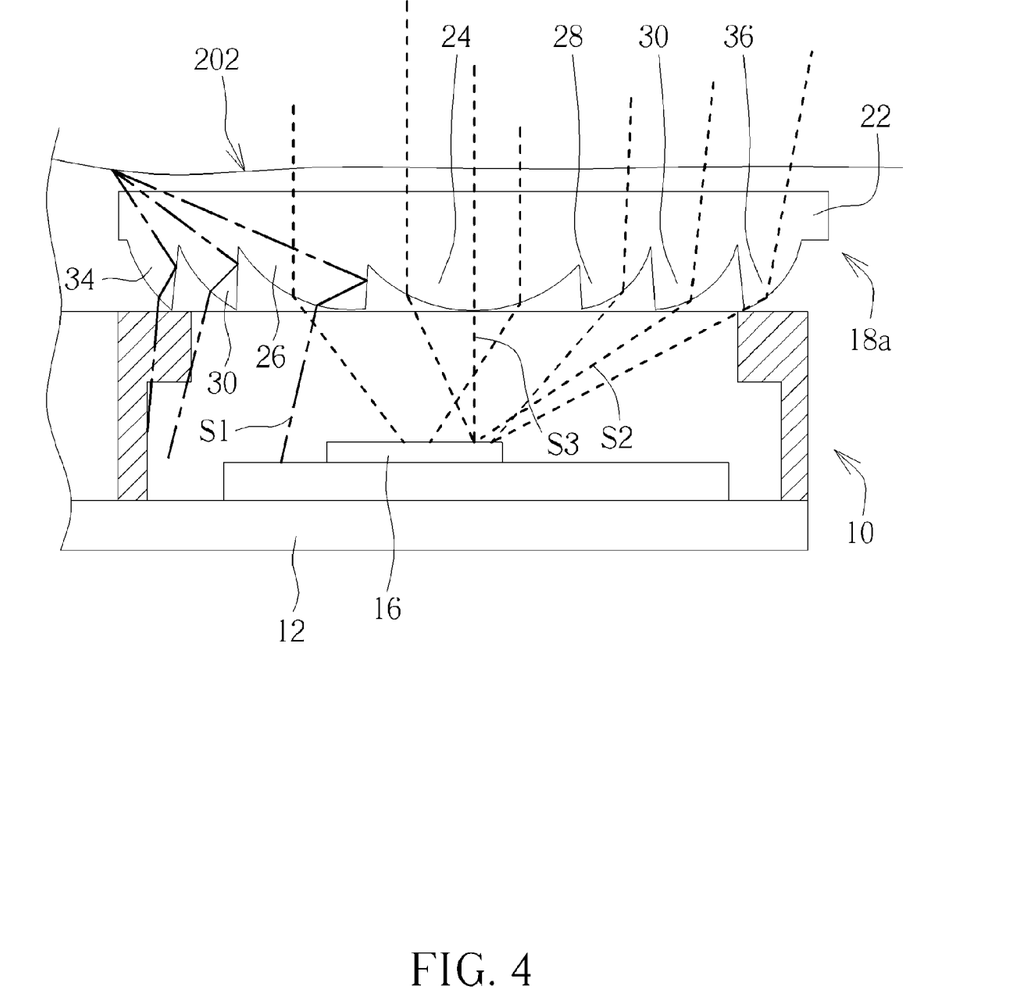
FIG. 4 is an enlarged diagram of the specific region shown in FIG. 3.

Please refer to FIG. 3 and FIG. 4. FIG. 3 is a diagram of an optical detecting device 10 according to an embodiment of the present invention. FIG. 4 is an enlarged diagram of the region A shown in FIG. 3. The optical detecting device 10 includes a substrate 12, a light emitting component 14, an optical detecting component 16 and a multi-segment optical component 18. The light emitting component 14 and the optical detecting component 16 are respectively disposed on different positions on the substrate 12. The light emitting component 14 faces outward of the optical detecting device 10 to project an optical detecting signal onto an external object 20. The optical detecting component 16 receives an optical reflecting signal from the external object 20, and analyzes information of the external object 20 according to photoplethysmography (PPG) of the optical signal. The external object 20 can be human skin, such as the finger or the wrist. The external object 20 may include an epidermal layer 201, a dermis layer 202 and a vessel 203. The optical detecting signal is projected onto the external object 20 to generate an epidermal scattering signal S1, a dermis scattering signal S2 and a vessel scattering signal S3. The optical detecting component 16 acquires vessel information of the external object 20 mainly by the vessel scattering signal S3.

The optical detecting device 10 disposes the multi-segment optical component 18 above the light emitting component 14 and/or the optical detecting component 16. The optical detecting signal output by the light emitting component 14 passes through the multi-segment optical component 18 to project onto the external object 20, and the optical detecting component 16 receives the optical reflecting signal back through the multi-segment optical component 18. The multi-segment optical component 18 can condense the optical detecting signal and isolate part of the optical reflecting signal, to avoid epidermal scattering influence and to improve the vessel scattering signal, so that signal-to-noise ratio (SNR) of the optical detecting device 10 can be increased accordingly. The multi-segment optical component 18 can be optionally designed as the multi-segment optical component 18a and the multi-segment optical component 18b which have similar structures. The multi-segment optical component 18a is preferably applied to the optical detecting component 16, and the multi-segment optical component 18b is preferably applied to the light emitting component 14; detailed structural characteristics are illustrated in the following description.

Figure 5:
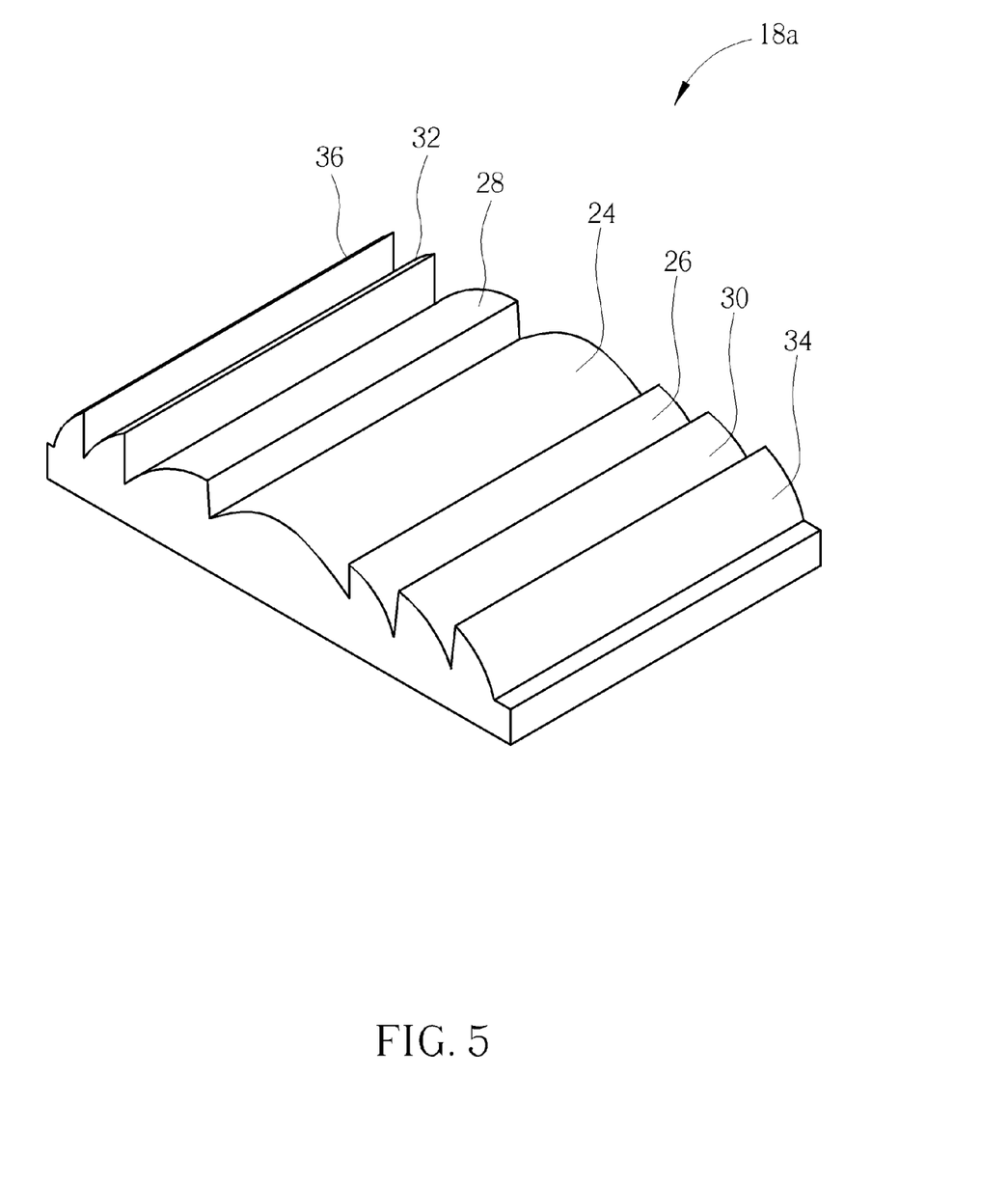
FIG. 5 is a diagram of the multi-segment optical component according to the embodiment of the present invention.
Figure 6:
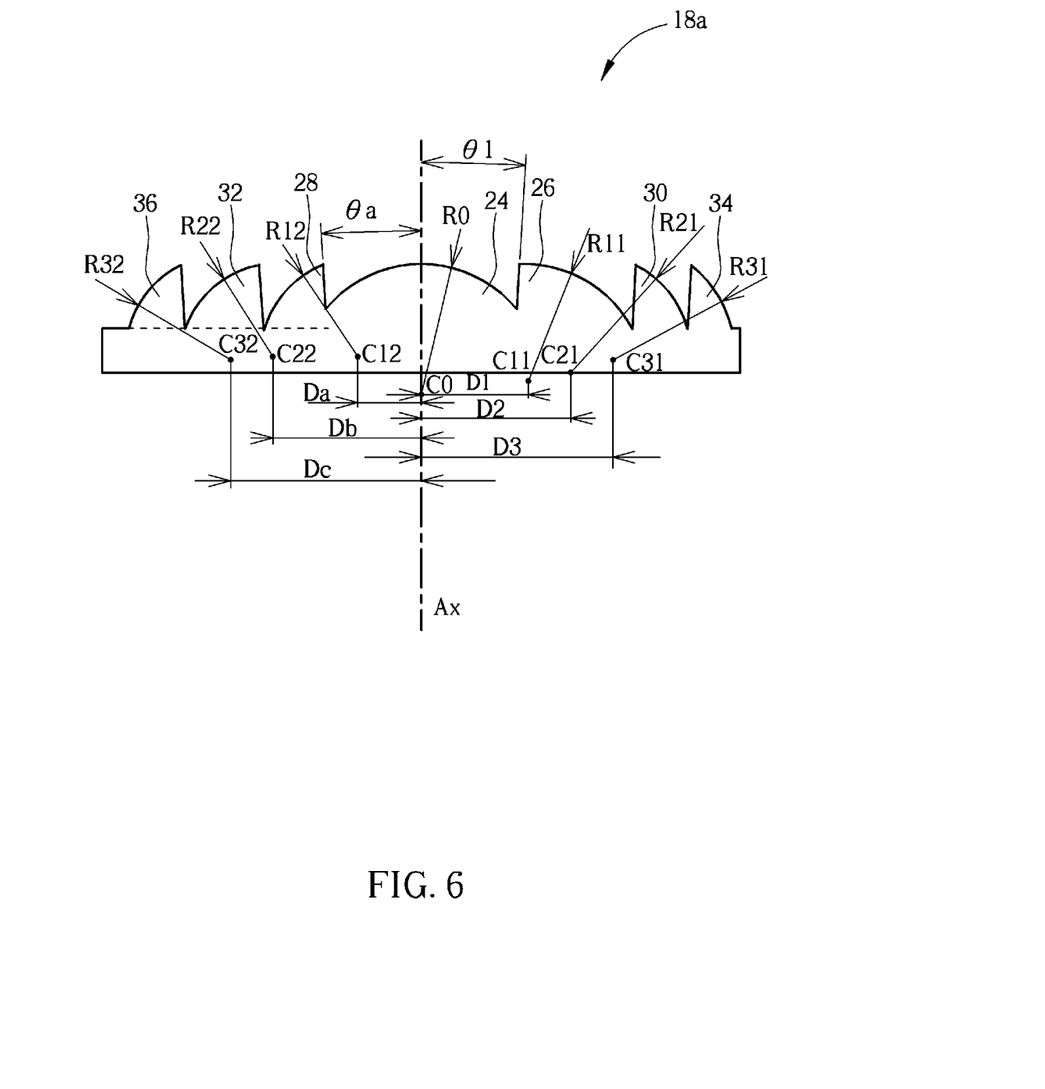
FIG. 6 is a sectional view of the multi-segment optical component according to the embodiment of the present invention.

Please refer to FIG. 3 to FIG. 6. FIG. 5 is a diagram of the multi-segment optical component 18a according to the embodiment of the present invention. FIG. 6 is a sectional view of the multi-segment optical component 18a according to the embodiment of the present invention. The multi-segment optical component 18a mainly includes a base 22, a central lens portion 24 and a plurality of lateral lens portions. The central lens portion 24 is disposed on center of the base 22, and the plurality of lateral lens portions is sequentially disposed by two sides of the central lens portion 24. In the embodiment, three sets of lateral lens portions are applied to the multi-segment optical component 18a, and actual application is not limited as above, which depends on design demand. For example, the first lateral lens portion may include a first isolating lens portion 26 and a first collecting lens portion 28; the first isolating lens portion 26 is disposed by a side of the central lens portion 24, and the first collecting lens portion 28 is disposed by the other side of the central lens portion 24 opposite to the first isolating lens portion 26. The second lateral lens portion may include a second isolating lens portion 30 and a second collecting lens portion 32 respectively disposed by sides of the first lateral lens portion opposite to the central lens portion 24. The third lateral lens portion may include a third isolating lens portion 34 and a third collecting lens portion 36 respectively disposed by sides of the second lateral lens portion opposite to the central lens portion 24.

The central lens portion 24 has a central axle Ax and a curvature radius R0. A curvature center C0 of the central lens portion 24 overlaps the central axle Ax. At least one of a curvature radius R11 of the first isolating lens portion 26 and a curvature radius R12 of the first collecting lens portion 28 is different from the curvature radius R0, and the curvature radius R11 can be the same as or different from the curvature radius R12 optionally. Thus, at least one of a curvature center C11 of the first isolating lens portion 26 and a curvature center C12 of the first collecting lens portion 28 does not overlap the central axle Ax. Generally, the curvature radius R11 of the first isolating lens portion 26 preferably can be, but not limited to, 0.86~0.97 times the curvature radius R0; the curvature radius R12 of the first collecting lens portion 28 preferably can be, but not limited to, 0.7~0.82 times the curvature radius R0.

Accordingly, at least one of a curvature radius R21 of the second isolating lens portion 30 and a curvature radius R22 of the second collecting lens portion 32 is different from the curvature radius R0, at least one of a curvature radius R31 of the third isolating lens portion 34 and a curvature radius R32 of the third collecting lens portion 36 is different from the curvature radius R0. At least one of the circle centers (which means the curvature center C21 and the curvature center C22) of the second lateral lens portion does not overlap the central axle Ax, at least one of the circle centers (which means the curvature center C31 and the curvature center C32) of the third lateral lens portion does not overlap the central axle Ax. In addition, the curvature radius R21 of the second isolating lens portion 30 is preferably 0.93~1.1 times the curvature radius R0, the curvature radius R22 of the second collecting lens portion is preferably 0.66~0.77 times the curvature radius R0, the curvature radius R31 of the third isolating lens portion 34 is preferably 0.91~1.0 times the curvature radius R0, and the curvature radius R32 of the third collecting lens portion 36 is preferably 0.78~0.89 times the curvature radius R0. Parameters setting are not limited to the above-mentioned data, which can be varied according to design demand.

As shown in FIG. 6, the curvature centers of all the lateral lens portions of the multi-segment optical component 18a do not overlap the central axle Ax. This embodiment further defines that a distance D2 between the curvature center C21 of the second isolating lens portion 30 and the central axle Ax is 1.2~1.6 times a distance D1 between the curvature center C11 of the first isolating lens portion 26 and the central axle Ax, a distance Db between the curvature center C22 of the second collecting lens portion 32 and the central axle Ax is 2.2~2.6 times a distance Da between the curvature center C12 of the first collecting lens portion 28 and the central axle Ax, a distance D3 between the curvature center C31 of the third isolating lens portion 34 and the central axle Ax is 1.6~2.0 times the distance D1 between the curvature center C11 of the first isolating lens portion 26 and the central axle Ax, a distance Dc between the curvature center C32 of the third collecting lens portion 36 and the central axle Ax is 2.8~3.2 times the distance Da between the curvature center C12 of the first collecting lens portion 28 and the central axle Ax; distance relation between the lateral lens portions and the central axle Ax are not limited to the above-mentioned application, which depend on actual demand.

It should be mentioned that an angle θ1 formed between a reflective surface 38 of the first isolating lens portion 26 and the central axle Ax can be substantially different from an angle θa formed between a reflective surface 40 of the first collecting lens portion 28 and the central axle Ax. Angles between the central axle Ax and reflective surfaces of the second isolating lens portion 30 and the second collecting lens portion 32 can be optionally different from each other, and angles between the central axle Ax and reflective surfaces of the third isolating lens portion 34 and the third collecting lens portion 36 can be optionally different from each other.

Figure 7:
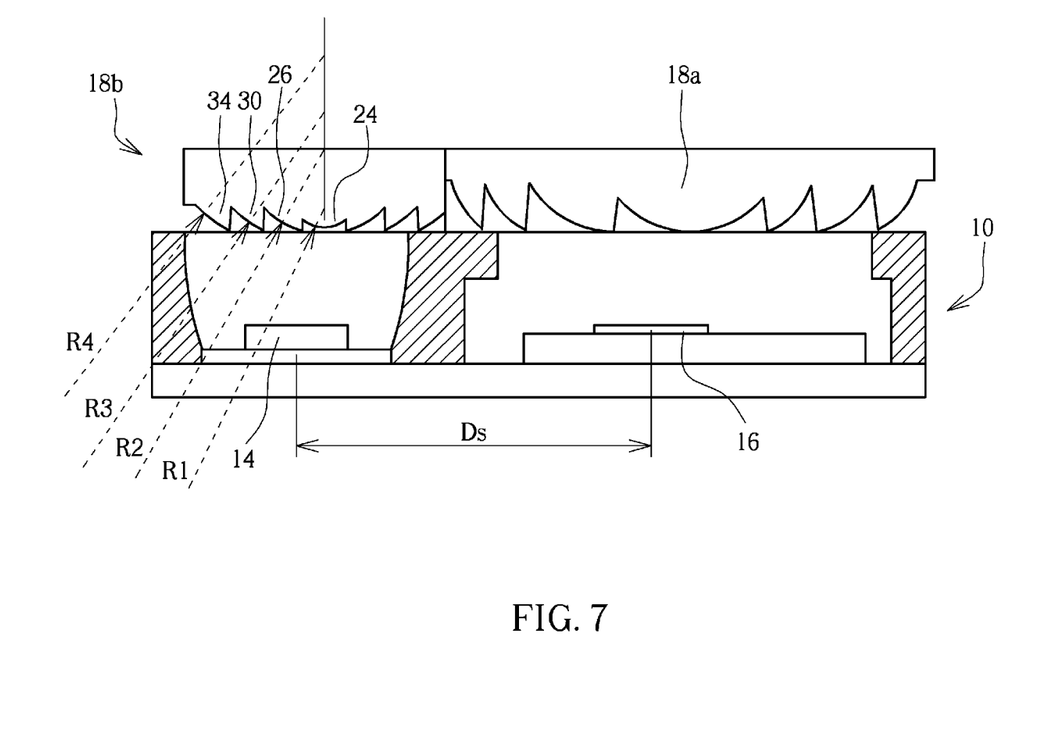
FIG. 7 is a diagram of the multi-segment optical component, the light emitting component and the optical detecting component according to the embodiment of the present invention.

Please refer to FIG. 7. FIG. 7 is a diagram of the multi-segment optical component 18b, the light emitting component 14 and the optical detecting component 16 according to the embodiment of the present invention. The optical detecting signal output by the light emitting component 14 can be focused within a specific range by the multi-segment optical component 18b, to decrease quantity of the epidermal scattering signal received by the optical detecting component 16. In this embodiment, a distance Ds between the light emitting component 14 and the optical detecting component 16 is defined, and the curvature radius R1 of the central lens portion 24 of the multi-segment optical component 18b is preferably 0.04~0.08 times the distance Ds. The curvature radius R2 of the first lateral lens portion (such as the first isolating lens portion 26 or the first collecting lens portion 28) of the multi-segment optical component 18b is preferably 0.2~0.26 times the distance Ds, the curvature radius R3 of the second lateral lens portion (such as the second isolating lens portion 30 or the second collecting lens portion 32) is preferably 0.33~0.4 times the distance Ds, and the curvature radius R4 of the third lateral lens portion (such as the third isolating lens portion 34 or the third collecting lens portion 36) is preferably 0.52~00.58 times the distance Ds.

The multi-segment optical component 18 of the present invention has the plurality of lateral lens portions with different curvature radii and the curvature centers not overlapping the central axle Ax. It is to say, the curvature radius R11 of the first isolating lens portion 26, the curvature radius R12 of the first collecting lens portion 28, the curvature radius R21 of the second isolating lens portion 30, the curvature radius R22 of the second collecting lens portion 32, the curvature radius R31 of the third isolating lens portion 34, and the curvature radius R32 of the third collecting lens portion 36 can be similar or dissimilar, which means at least one or more of the curvature radii of those isolating lens portions and collecting lens portions are different from the curvature radius R0 of the central lens portion 24. The curvature center C11 of the first isolating lens portion 26, the curvature center C12 of the first collecting lens portion 28, the curvature center C21 of the second isolating lens portion 30, the curvature center C22 of the second collecting lens portion 32, the curvature center C31 of the third isolating lens portion 34, and the curvature center C32 of the third collecting lens portion 36 may overlap or not overlap the central axle Ax; at least one or more of those curvature centers do not overlap the central axle Ax.

The present invention disposes the multi-segment optical components 18 with different types respectively on the light emitting component 14 and the optical detecting component 16. While the multi-segment optical component 18a is disposed above the optical detecting component 16, the optical detecting component 16 aligns with a region of the central lens portion 24 near to the first isolating lens portion 26 of the multi-segment optical component 18a, to obstruct the epidermal scattering signal S1 generated by the epidermal layer 201 via scattering isolation module (which includes the first isolating lens portion 26, the second isolating lens portion 30 and the third isolating lens portion 34), and further to increase collection quantity of the vessel scattering signal S3 and/or the dermis scattering signal S2 via the optical collection module (which includes the first collecting lens portion 28, the second collecting lens portion 32 and the third collecting lens portion 36), as shown in FIG. 4. While the multi-segment optical component 18b is disposed above the light emitting component 14, the multi-segment optical component 18b is near to the optical detecting component 16, which can be shown in FIG. 7, so as to narrow wide-angle illumination of the light emitting component 14 within the specific range and to decrease the quantity of the epidermal scattering signal S1 received by the optical detecting component 16.

Comparing to the prior art, the present invention provides the innovative multi-segment optical component distinct from the conventional Fresnel lens. All the lateral lens portions of the multi-segment optical component have curvature radii different from the curvature radius of the central lens portion, and the curvature centers of all the lateral lens portions do not overlap the central axle of the central lens portion. Therefore, the multi-segment optical component can utilize the scattering isolation module to prevent the epidermal scattering signal from being transmitted toward the optical detecting component, and further utilize the optical collection module to collect the vessel scattering signal and/or the dermis scattering signal, so as to effectively increase the signal-to-noise ratio of the optical detecting device; the optical detecting device of the present invention can acquire accurate detecting result even through the external object does not directly contact an effective region (the working region, the touch region) of the optical detecting device.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:
1. A multi-segment optical component capable of increasing signal-to-noise ratio (SNR), the multi-segment optical component comprising:
    a base;
    a central lens portion disposed on center of the base;
    a first isolating lens portion disposed by a side of the central lens portion; and a first collecting lens portion disposed by the other side of the central lens portion opposite to the first isolating lens portion;
wherein at least one of the first isolating lens portion and the first collecting lens portion has a curvature radius different from a curvature radius of the central lens portion.

2. The multi-segment optical component of claim 1, wherein the curvature radius of the first isolating lens portion is similar to or different from the curvature radius of the first collecting lens portion.

3. The multi-segment optical component of claim 1, wherein the curvature radius of the first isolating lens portion is 0.86~0.97 times the curvature radius of the central lens portion, and/or the curvature radius of the first collecting lens portion is 0.7~0.82 times the curvature radius of the central lens portion.

4. The multi-segment optical component of claim 1, wherein the central lens portion comprises a central axle, at least one of the first isolating lens portion and the first collecting lens portion has a curvature center not overlapping the central axle.

5. The multi-segment optical component of claim 4, further comprising:
a second isolating lens portion disposed by a side of the first isolating lens portion opposite to the central lens portion; and
a second collecting lens portion disposed by a side of the first collecting lens portion opposite to the central lens portion;
wherein at least one of the second isolating lens portion and the second collecting lens portion has a curvature radius different from the curvature radius of the central lens portion.

6. The multi-segment optical component of claim 5, wherein the curvature radius of the second isolating lens portion is 0.93~1.1 times the curvature radius of the central lens portion, and/or the curvature radius of the second collecting lens portion is 0.66~0.77 times the curvature radius of the central lens portion.

7. The multi-segment optical component of claim 5, wherein a distance between a curvature center of the second isolating lens portion and the central axle is 1.2~1.6 times a distance between the curvature center of the first isolating lens portion and the central axle, and/or a distance between a curvature center of the second collecting lens portion and the central axle is 2.2~2.6 times a distance between the curvature center of the first collecting lens portion and the central axle.

8. The multi-segment optical component of claim 5, further comprising:
a third isolating lens portion disposed by a side of the second isolating lens portion opposite to the central lens portion; and
a third collecting lens portion disposed by a side of the second collecting lens portion opposite to the central lens portion;
wherein at least one of the third isolating lens portion and the third collecting lens portion has a curvature radius different from the curvature radius of the central lens portion.

9. The multi-segment optical component of claim 8, wherein the curvature radius of the third isolating lens portion is 0.91~1.0 times the curvature radius of the central lens portion, and/or the curvature radius of the third collecting lens portion is 0.78~0.89 times the curvature radius of the central lens portion.

10. The multi-segment optical component of claim 8, wherein a distance between a curvature center of the third isolating lens portion and the central axle is 1.6~2.0 times a distance between the curvature center of the first isolating lens portion and the central axle, and/or a distance between a curvature center of the third collecting lens portion and the central axle is 2.8~3.2 times a distance between the curvature center of the first collecting lens portion and the central axle.

11. The multi-segment optical component of claim 4, wherein an angle formed between a reflective surface of the first isolating lens portion and the central axle is different from an angle formed between a reflective surface of the first collecting lens portion and the central axle.

12. An optical detecting device capable of increasing signal-to-noise ratio (SNR), the optical detecting device comprising:
a light emitting component adapted to emit an optical detecting signal toward an external object;
an optical detecting component adapted to receive an optical reflecting signal from the external object; and
at least one multi-segment optical component disposed on the light emitting component and/or the optical detecting component, and adapted to condense the optical detecting signal and/or isolate part of the optical reflecting signal, the at least one multi-segment optical component comprising:
a base;
a central lens portion disposed on center of the base;
a first isolating lens portion disposed by a side of the central lens portion; and
a first collecting lens portion disposed by the other side of the central lens portion opposite to the first isolating lens portion;
wherein at least one of the first isolating lens portion and the first collecting lens portion has a curvature radius different from a curvature radius of the central lens portion.

13. The optical detecting device of claim 12, wherein the curvature radius of the first isolating lens portion is similar to or different from the curvature radius of the first collecting lens portion.

14. The optical detecting device of claim 12, wherein the curvature radius of the first isolating lens portion is 0.86~0.97 times the curvature radius of the central lens portion, and/or the curvature radius of the first collecting lens portion is 0.7~0.82 times the curvature radius of the central lens portion.

15. The optical detecting device of claim 12, wherein the central lens portion comprises a central axle, at least one of the first isolating lens portion and the first collecting lens portion has a curvature center not overlapping the central axle.

16. The optical detecting device of claim 15, wherein the multi-segment optical component further comprises:
a second isolating lens portion disposed by a side of the first isolating lens portion opposite to the central lens portion; and
a second collecting lens portion disposed by a side of the first collecting lens portion opposite to the central lens portion;
wherein at least one of the second isolating lens portion and the second collecting lens portion has a curvature radius different from the curvature radius of the central lens portion.

17. The optical detecting device of claim 16, wherein the curvature radius of the second isolating lens portion is 0.93~1.1 times the curvature radius of the central lens portion, and/or the curvature radius of the second collecting lens portion is 0.66~0.77 times the curvature radius of the central lens portion.

18. The optical detecting device of claim 16, wherein a distance between a curvature center of the second isolating lens portion and the central axle is 1.2~1.6 times a distance between the curvature center of the first isolating lens portion and the central axle, and/or a distance between a curvature center of the second collecting lens portion and the central axle is 2.2~2.6 times a distance between the curvature center of the first collecting lens portion and the central axle.

19. The optical detecting device of claim 16, wherein the multi-segment optical component further comprises:
- a third isolating lens portion disposed by a side of the second isolating lens portion opposite to the central lens portion; and
- a third collecting lens portion disposed by a side of the second collecting lens portion opposite to the central lens portion;
- wherein at least one of the third isolating lens portion and the third collecting lens portion has a curvature radius different from the curvature radius of the central lens portion.

20. The optical detecting device of claim 19, wherein the curvature radius of the third isolating lens portion is 0.91~1.0 times the curvature radius of the central lens portion, and/or the curvature radius of the third collecting lens portion is 0.78~0.89 times the curvature radius of the central lens portion.

21. The optical detecting device of claim 19, wherein a distance between a curvature center of the third isolating lens portion and the central axle is 1.6~2.0 times a distance between the curvature center of the first isolating lens portion and the central axle, and/or a distance between a curvature center of the third collecting lens portion and the central axle is 2.8~3.2 times a distance between the curvature center of the first collecting lens portion and the central axle.

22. The optical detecting device of claim 15, wherein an angle formed between a reflective surface of the first isolating lens portion and the central axle is different from an angle formed between a reflective surface of the first collecting lens portion and the central axle.

23. The optical detecting device of claim 12, wherein when the at least one multi-segment optical component is disposed above the optical detecting component, the optical detecting component aligns with a region of the central lens portion near to the first isolating lens portion of the at least one multi-segment optical component.

24. The optical detecting device of claim 12, wherein the at least one multi-segment optical component is disposed above a region of the light emitting component near to the optical detecting component.

25. The optical detecting device of claim 12, wherein when the at least one multi-segment optical component is disposed above the light emitting component, the curvature radius of the central lens portion is 0.04~0.08 times a distance between the light emitting component and the optical detecting component.

26. The optical detecting device of claim 12, wherein when the at least one multi-segment optical component is disposed above the light emitting component, the curvature radius of the first collecting lens portion is 0.2~0.26 times a distance between the light emitting component and the optical detecting component.

27. The optical detecting device of claim 16, wherein when the at least one multi-segment optical component is disposed above the light emitting component, the curvature radius of the second collecting lens portion is 0.33~0.4 times a distance between the light emitting component and the optical detecting component.

28. The optical detecting device of claim 19, wherein when the at least one multi-segment optical component is disposed above the light emitting component, the curvature radius of the third collecting lens portion is 0.52~0.58 times a distance between the light emitting component and the optical detecting component.

* * * * *